(12) United States Patent
Bajikar et al.

(10) Patent No.: US 7,921,731 B2
(45) Date of Patent: Apr. 12, 2011

(54) TWO-AXIS DIRECT FLUID SHEAR STRESS SENSOR

(75) Inventors: Sateesh Bajikar, San Jose, CA (US); Michael A. Scott, Newport News, VA (US); Edward E. Adcock, Poquoson, VA (US)

(73) Assignee: The United States of America as represented by the Administrator of the National Aeronautics and Space Administration, Washington, DC (US)

(*) Notice: Subject to any disclaimer, the term of this patent is extended or adjusted under 35 U.S.C. 154(b) by 183 days.

(21) Appl. No.: 12/327,514

(22) Filed: Dec. 3, 2008

(65) Prior Publication Data
US 2009/0223302 A1    Sep. 10, 2009

Related U.S. Application Data

(60) Provisional application No. 60/991,975, filed on Dec. 3, 2007.

(51) Int. Cl.
*G01N 3/24* (2006.01)
(52) U.S. Cl. .......................................... 73/841; 73/760
(58) Field of Classification Search .................. 73/760, 73/841
See application file for complete search history.

(56) References Cited

U.S. PATENT DOCUMENTS

| | | | |
|---|---|---|---|
| 4,598,585 A | 7/1986 | Boxenhorn | |
| 4,699,006 A | 10/1987 | Boxenhorn | |
| 4,739,381 A | 4/1988 | Miura et al. | |
| 4,896,098 A | 1/1990 | Haritonidis et al. | |
| 5,199,298 A | 4/1993 | Ng et al. | |
| 5,203,208 A | 4/1993 | Bernstein | |
| 5,220,835 A | 6/1993 | Stephan | |
| 5,648,618 A | 7/1997 | Neukermans et al. | |
| 5,895,866 A | 4/1999 | Neukermans et al. | |
| 6,253,626 B1* | 7/2001 | Shoberg et al. | 73/862.044 |
| 6,279,393 B1* | 8/2001 | McLaughlin | 73/170.14 |
| 6,408,698 B1 | 6/2002 | Brereton et al. | |
| 6,426,796 B1 | 7/2002 | Pulliam et al. | |
| 6,580,418 B1* | 6/2003 | Grome et al. | 345/161 |
| 6,966,231 B2 | 11/2005 | Sheplak et al. | |

* cited by examiner

*Primary Examiner* — Max Noori
(74) *Attorney, Agent, or Firm* — Matthew F. Johnston

(57) ABSTRACT

A micro sized multi-axis semiconductor skin friction/wall shear stress induced by fluid flow. The sensor design includes a shear/strain transduction gimble connected to a force collecting plate located at the flow boundary surface. The shear force collecting plate is interconnected by an arm to offset the tortional hinges from the fluid flow. The arm is connected to the shear force collecting plate through dual axis torsional hinges with piezoresistive torsional strain gauges. These gauges are disposed on the tortional hinges and provide a voltage output indicative of applied shear stress acting on the force collection plate proximate the flow boundary surface. Offsetting the torsional hinges creates a force concentration and resolution structure that enables the generation of a large stress on the strain gauge from small shear stress, or small displacement of the collecting plate. The design also isolates the torsional sensors from exposure to the fluid flow.

8 Claims, 4 Drawing Sheets

FIG. 3
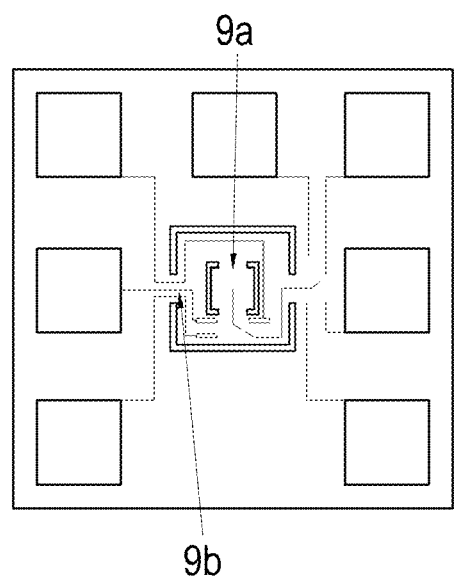
FIG. 4
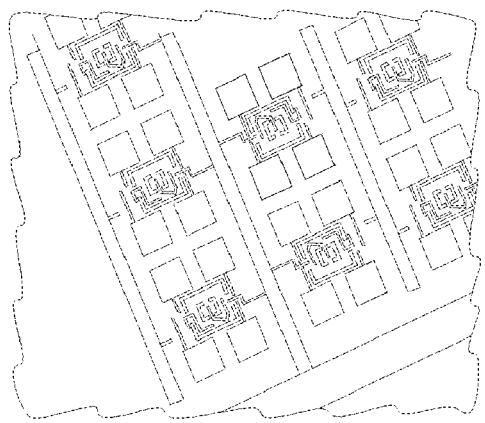
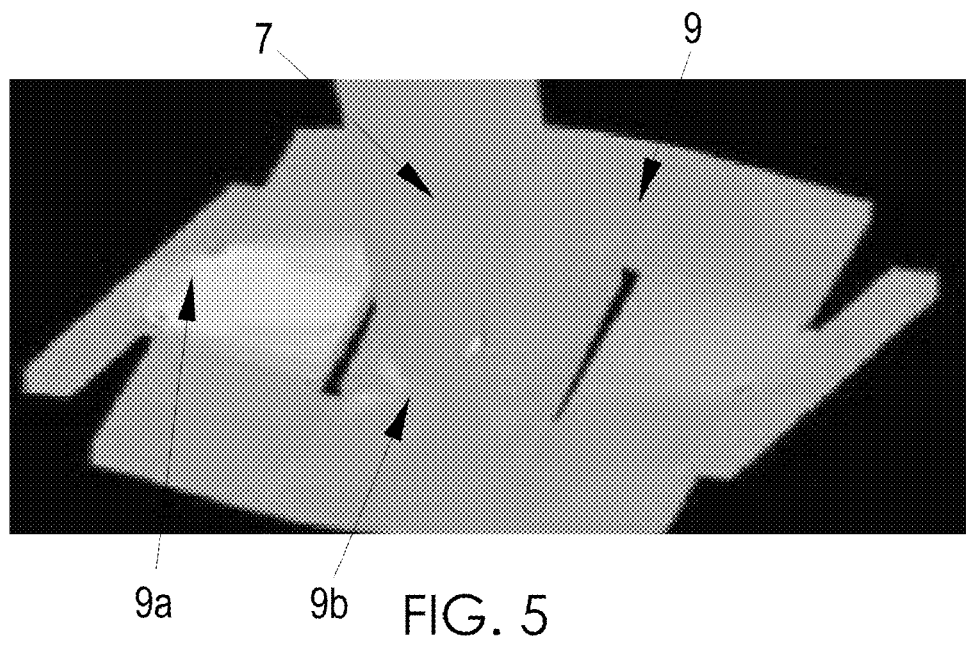
FIG. 5

TWO-AXIS DIRECT FLUID SHEAR STRESS SENSOR

RELATED APPLICATIONS

This application is based upon a prior filed provisional patent application Ser. No. 60/991,975 filed Dec. 3, 2007, entitled "A TWO AXIS DIRECT FLUID SHEAR STRESS SENSOR SUITED FOR AERODYNAMIC APPLICATIONS", the entire subject matter of which is incorporated herein by reference.

GOVERNMENT INTEREST

The embodiments of the invention described herein were made by employees of the United States Government, and may be manufactured and used by or for the United States Government for governmental purposes without payment of any royalties thereon or therefor.

BACKGROUND OF THE INVENTION

1. Field of the Invention

The present invention relates to shear stress sensors and more particularly to a micro sized multi-axis semiconductor skin friction/wall shear stress sensor/devices.

2. Description of the Related Art

A great number of techniques for the measurement of wall shear stress exist within the prior art, ranging from inferring the skin friction from measuring the boundary layer profile or using some correlation or analogy to the direct measurement of the force on a surface. Although all of these techniques can be shown to accommodate some flow regimes, indirect methods have not been shown to be reliable for complex flows, high-speed flows, or flows associated with combustion and/or impinging shocks. Alternatively, direct measurements do not require any foreknowledge of the flow or its properties and can provide accurate results all the regimes mentioned above.

Direct measurements, refers to techniques that separate a small element, referred to as a floating head, from the wall and measures the tangential force that the flow imparts on it. Direct measurements are the most believable of all the techniques. The sensor is measuring the actual shear on the surface, without respect to the fluid, the state of the boundary layer, or Reynolds Number. Since the floating head is level with the wall, the measurement is non-intrusive to the flow. The forces are very small, sometimes requiring large floating heads and expensive instrumentation to obtain accurate results. A variety of such direct shear stress sensors are also known in the art. One type of direct shear stress sensor is a floating element sensor such as disclosed in U.S. Pat. No. 4,896,098 incorporated herein by reference. Other flow sensors include those disclosed in U.S. Pat. Nos. 6,966,231; 6,408,698; 5,199,209 the entire contents of which are each incorporated herein by reference. These floating sensors are exposed to the fluid flow and thus are not suitable for extreme or hostile conditions and often require complex optical or capacitive transduction techniques. Another floating element shear-stress sensor employed differential optical-shutter-based floating element sensors for turbulence measurements such as disclosed in U.S. Pat. No. 6,426,796 the entire disclosure of which is incorporated herein by reference. However, the performance of this sensor suffers from front-side electrical contacts that interfere with fluid flow past the sensor and/or from remote mounting of the incident light source.

The measurement of shear stress is of importance in a large number of situations involving fluid flow, including aerodynamic, hydrodynamics, turbo machinery, and polymer processing among several others. Quantifying shear stress is important in order to understand and control the flow and in particular to control and suppress the development of turbulence in it. The magnitude of the shear stress and needed resolution in these various situations can span many orders from milliPascals to kiloPascal or more. The frequency response and spatial resolution needed also varies considerably. Both direct and indirect principles for sensing this shear force and sensors employing these exist with the direct methods being favored, however no commercial devices are readily available. The demands of sensors for aerodynamic application are in particular very challenging to meet as the forces involved are small (few Pascal to few hundred Pascal) and the resolution needed is high (few milliPascal) with high spatial resolution (few hundred microns or less) and frequency response from steady state to tens of kilohertz. There is also the need for directional information and the ability to array large numbers of such sensors to collect this information over the area of interest. The present invention is a micro sensor that is ideally suited for such this application and can fabricated using MEMS (Micro Electro Mechanical Systems) fabrication techniques. It is however not limited this application and can find use in the above mentioned or in other situations by a suitable choice of design parameters.

SUMMARY OF THE INVENTION

The present invention is directed to a multi-axis direct shear stress sensor. The sensor includes a shear force collecting plate mounted substantially flush and coplanar with an adjacent associated wall exposed to fluid flow. A gimbal structure including an arm connects the shear force collecting plate to a multi-axis torsional sensor to facilitate pivotal movement of the plate relative to the sensor in response to fluid flow across the collecting plate. Pivotal movement of the shear force collecting plate causes deformation of said torsional sensor thereby inducing said torsional strain therein. The strain in the torsional sensor is directly indicative of the shear stress on the collecting plate.

BRIEF DESCRIPTION OF THE DRAWINGS

FIG. 3 is a bottom view of the Shear Stress Sensor, depicting the torsional sensor with integrated hinges according to the present invention.

FIG. 4 is a top view of an array of the torsional sensors of FIG. 3.

FIG. 5 is an isolate graphic perspective view of the torsional sensor and integrated hinged connected to the arm in a deformed position according to the present invention.

DETAILED DESCRIPTION OF A PREFERRED EMBODIMENT

Figure 1:
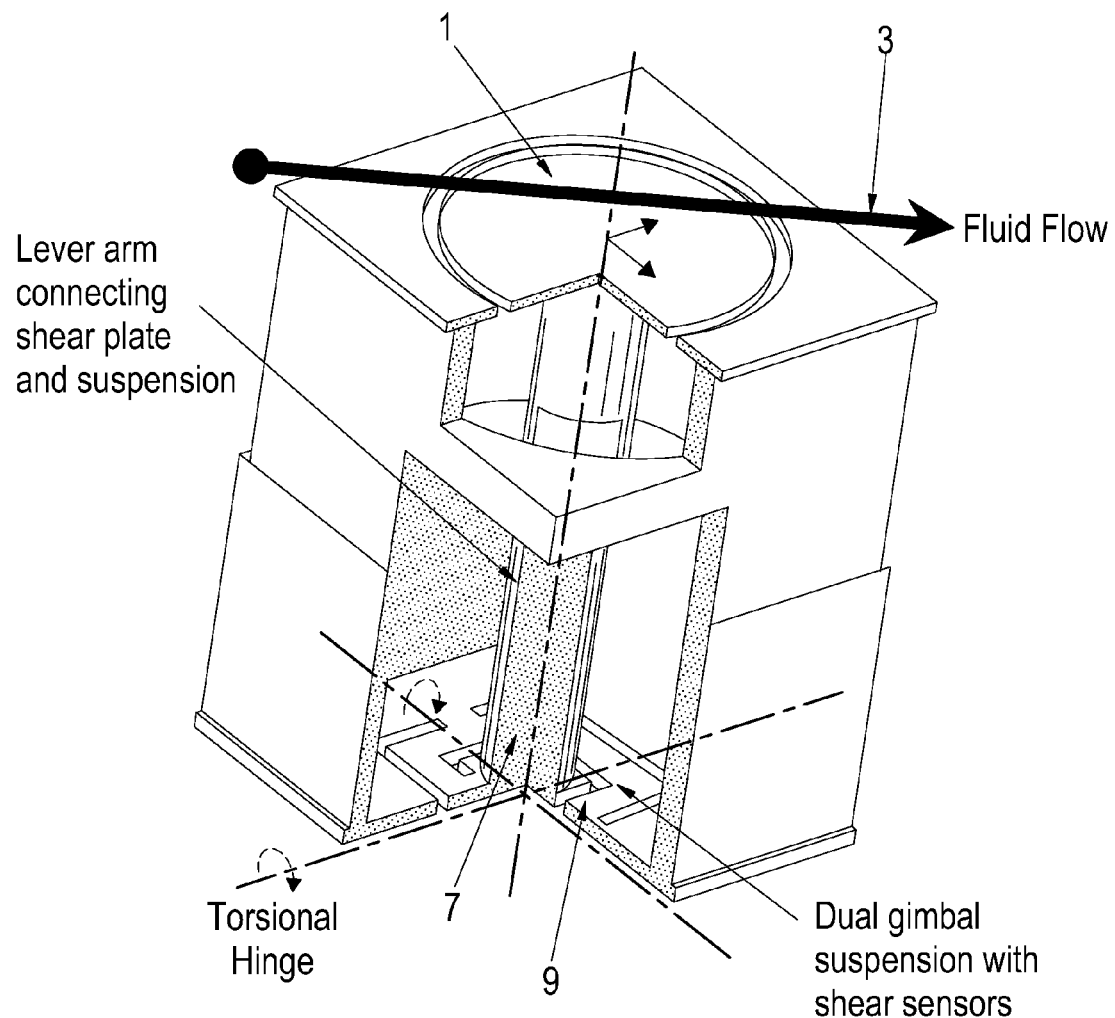
FIG. 1 is a graphic partial cut-away perspective view of the sensor assembly according to one embodiment of the present invention.

A preferred embodiment of the invention and the various features and advantageous details thereof are explained more fully with reference to the accompanying drawings and detailed in the following description. It should be noted that the features illustrated in the drawings are not necessarily drawn to scale and descriptions of well-known components and processing techniques are omitted so as to not unnecessarily obscure the embodiments of the invention. The examples used herein are intended merely to facilitate an understanding of ways in which the embodiments of the invention may be practiced and to further enable those of skill in the art to practice the embodiments of the invention. Accordingly, the examples should not be construed as limiting the scope of the embodiments of the invention.

Figure 2:
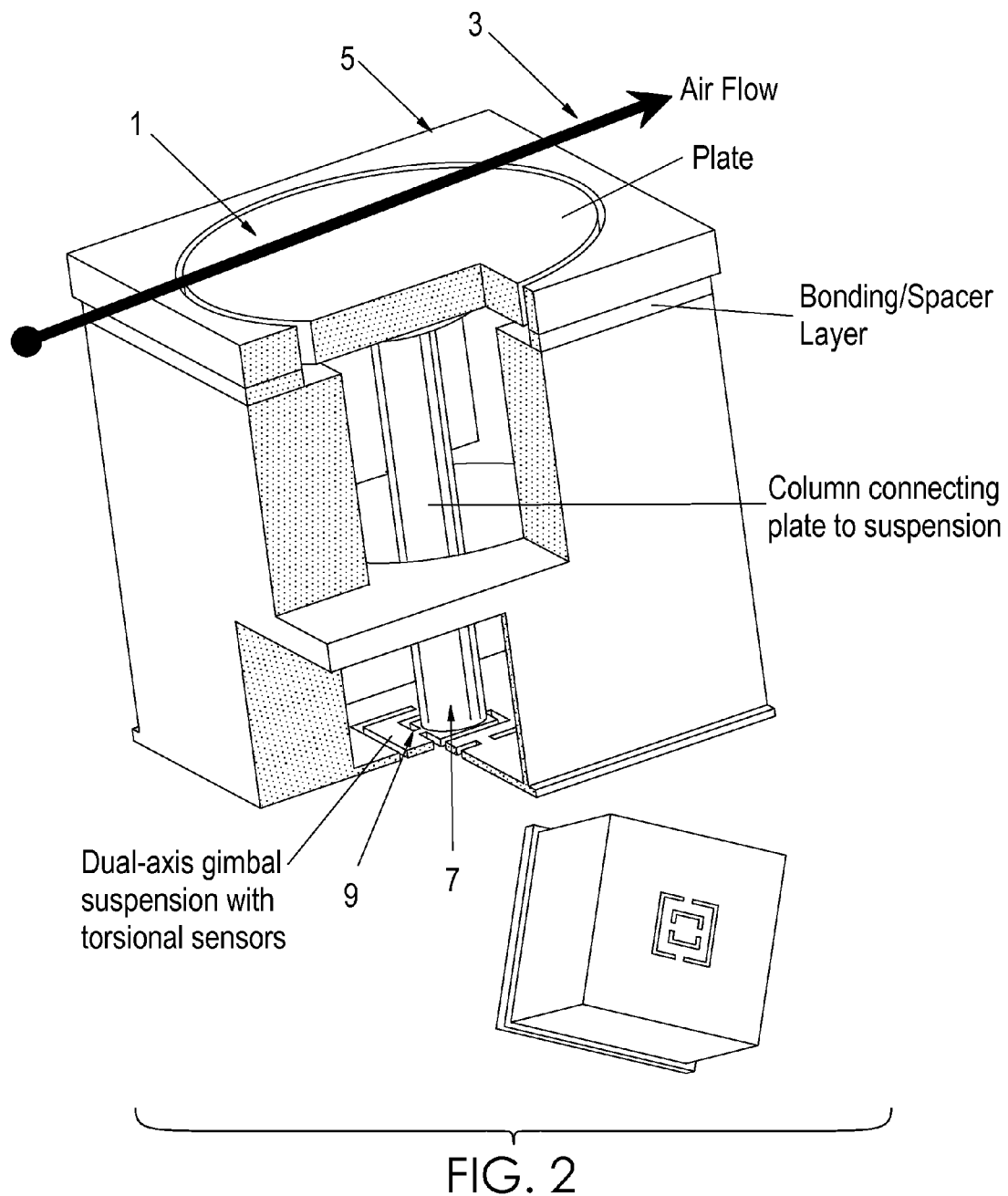
FIG. 2 is a graphic partial cut-away perspective view of the sensor assembly according to an alternate embodiment of the present invention.

FIGS. 1-2 depict partial cut away views of the sensor assembly according to the present invention. The sensor includes a shear force collected plate 1 that collects the shear force induced by fluid flow 3 and is of a dimension comparable to the needed spatial resolution (10 to 100 to 1000s of microns depending on application). Its surface is coplanar and flush with the surface of the device body 5 in order to enable non-intrusive or non disruptive mounting in the flow being measured. This plate is coupled to an arm 7 of a two axis gimbal structure 9. These gimbals are torsional hinges and permit rotation of the arm (and plate) about both axes of the gimbal plane. This structure, consisting of the plate 1, arm 7, and gimbal 9, are designed such that the tilt of the plate does not impact the macroscopic flow parameters. The hinges 9 and the entire device are fabricated of single crystal silicon and accommodate on their face piezoresistive torsional sensors. The sensor structure is shown in FIGS. 3-6. The sensor provides, upon excitation with a suitable electrical current (FIG. 7) through terminals 11 and 12, an output electrical signal (FIG. 7) across terminals 13 and 14, proportional to the shear stress experienced by the hinge 9. The sensors themselves are typically made by doping the silicon (by ion implantation or other means) to a suitable type and level of conductivity that provides the desired sensitivity depending on the crystal orientation and confines the excitation current to the sensor. Metallic electrical leads (shown in FIG. 6) on the back face of the device are provided to route excitation currents and output signal voltages from these sensors to the external world. Subjecting the shear force collecting plate 1 to a shear force by mounting it on an aerodynamic surface exposed to flow 3 will result in a moment acting on the hinges that is proportional to the shear stress on the plate 1, arm 7 and torsional hinge 9a,9b dimensions. This moment creates a mechanical torsional shear stress within the hinges 9a,9b and thereby an output signal proportional to the shear stress on the plate 1 from the piezoresistive sensor. The shear stress at the fluid-sensor interface is thus initially converted to a mechanical shear stress in the hinge 9 that is sensed with a piezoresistive sensor. The two orthogonally located hinges 9a,9b and sensors enable measuring the shear stress existing on the plate 1 in both directions. This configuration of the sensor device enables a large moment and stress level to be generated at the hinge from relatively small shear stress acting on a small plate thereby enabling high spatial and stress resolution capability. The location of the piezoresistive sensor on the rear face of the device enables wiring in a non-intrusive manner. That is to say, all electrical contacts are below the flow surface. The entire device may be fabricated in single crystal silicon using two silicon or SOI (Silicon-On-Insulator) wafers. Large arrays of sensors can be thus fabricated.

The sensor is fabricated by bonding together two partially structured wafers. The first is processed to first define the piezoresistive structures and metallic leads for these, using standard semiconductor ion implantation, deposition, lithography and etch techniques. The lever structure on the back side of this wafer is defined using photolithography and a deep silicon reactive ion etch using the BOSCH process that stops on the buried oxide layer if present or is timed to desired depth. The second wafer is similarly processed to define plate or lever (lever optional depending on process and design), on its backside. The two wafers are aligned and bonded at a modest temperature and pressure compatible with the metals and other materials used, using an intermediary layer such as a polymer (eg. BCB, polyimide, negative photoresist; metal. Gold-gold/Si-gold eutectic) or glass. Additional lithography and silicon reactive ion etching steps define the plate and the hinge and gimbal on either side of the bonded wafers and completes the sensor. Several of these sensors, of varying sensitivity and spatial resolution, have been fabricated and characterized. Furthermore, it may be possible, together with the teaching of the present invention, to glean additional torsional hinge arrangements from the teachings of micro machined torsional sensors employed in accelerometers such as those disclose in U.S. Pat. Nos. 5,648,618; 5,220,835; 4,598,585; 4,739,381; 4,699,006; 5,203,208; 5,895,866; the entire contents of each of which are incorporated herein by reference.

The sensor assembly of the present invention facilitates direct detection of wall shear stress independent of flow conditions with the transduction elements/piezoactive resistors/strain gauges being isolated from the fluid environment to provide the ability for applications in high/low temperature environments. The resultant assembly yields a substantially non-intrusive sensor with the active parts isolated from the environment thus enabling application in aircraft wings, watercraft surfaces etc. The assembly further enables active flow control and detecting the onset of turbulence which can be used to control actuators to modify the flow, drag reduction, separation delay or change the entire flow geometry. Conventional sensor assemblies are unable to meet these requirements.

FIG. 3 depicts a graphic finite element analysis model of an isolated view of a torsional sensor in a deformed position. The sensor is deformed in a single direction as reflected by a flow substantially along a single (x) axis. The arm creates a moment about the hinge such that IPA wind shear/skin friction load across the collecting plates yields 30-35 KPa on the hinge thus magnifying the stress/strain in the hinge. This results in the ability to more finely measure the shear stress on the collecting plate.

Figure 6:
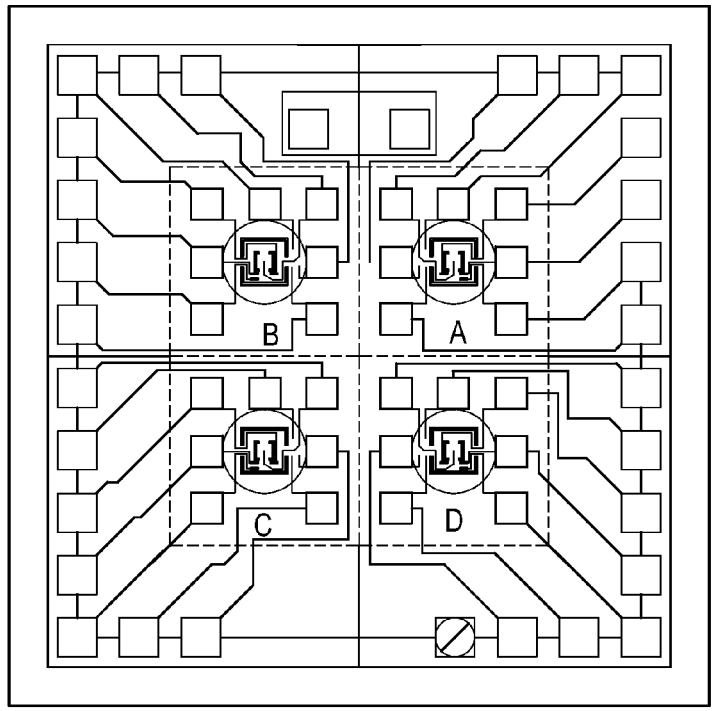
FIG. 6 is an electrical diagram of a two by two array of torsional sensors according to the present invention.
Figure 7:
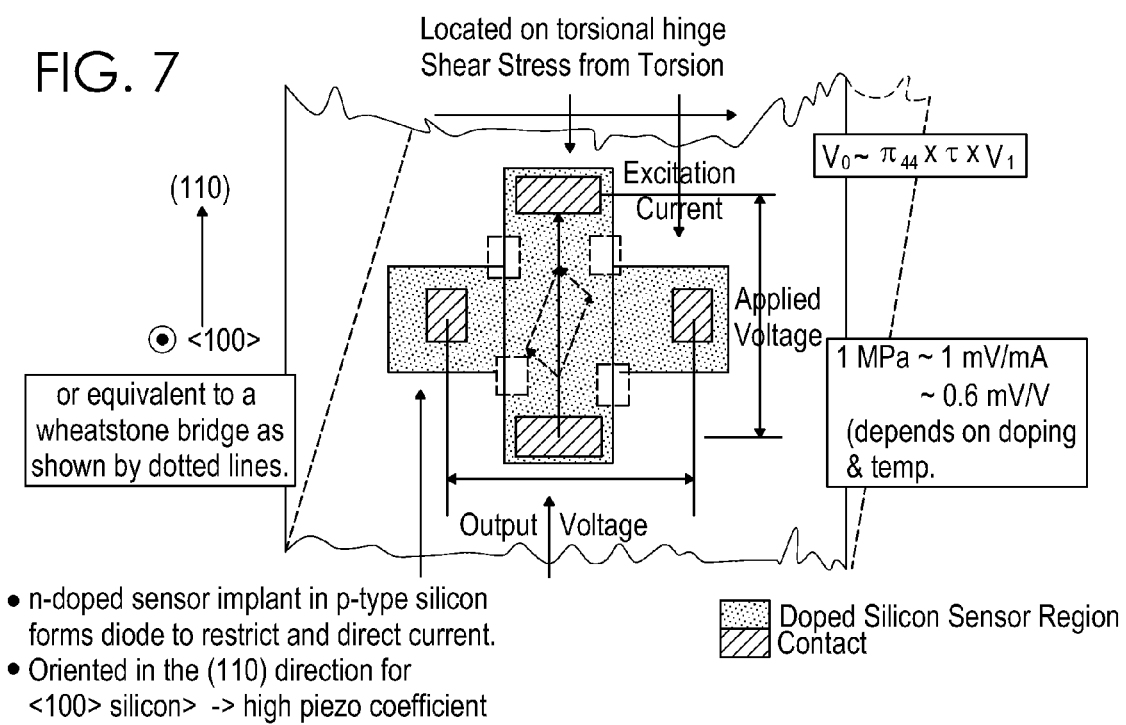
FIG. 7 is a schematic view of a single torsional sensor according to the present invention.

FIG. 6 presents one preferred embodiment wherein four sensors (2×2) are packaged in a single die having dimensions of 3.5 mm×3.5 mm. Each of the two axis sensors are electrically isolated from each other as well as a temperature sensor which has also been integrated into the die package. To sets of bonding pads are employed each electrically isolated. Other arranges have included/been fabricated an array of 64 sensors (8×8) wherein the collecting plate has a diameter if 430 μm, and array of 60 sensors (3×20) having a plate diameter of 179 μm, or an array of 100 sensors (10×100) having a plate diameter if 340 μm. In each of these embodiments the collecting plate has a thickness of 10 μm, the arm/column has a length of 400 μm and a diameter of 40 μm. The hinges dimensions are 36 μm by 5 μm. The appendix attached hereto includes structural details and test analysis data of a torsional sensor according to an embodiment of the present invention the entire contents of which are hereby incorporated herein by reference.

The foregoing description of the specific embodiments will so fully reveal the general nature of the invention that others can, by applying current knowledge, readily modify and or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments of the invention have been described in terms of preferred embodiments, those skilled in the art will recognize that the embodiments of the invention can be practiced with modification within the spirit and scope of the appended claims.

What is claimed is:

1. A multi-axis direct shear stress sensor comprising:
a shear force collecting plate mounted substantially flush and coplanar with an adjacent associated wall exposed to fluid flow;
a multi-axis torsional sensor to measure torsional strain about at least two axis;
a gimbal structure including an arm interconnecting said shear force collecting plate and said multi-axis torsional sensor to thereby facilitate pivotal movement of said shear force collecting plate in response to fluid flow across a surface thereof; wherein said pivotal movement of said shear force collecting plate causes deformation of said torsional sensor thereby inducing said torsional strain therein.

2. The sensor according to claim 1, wherein arm has a length of at least 400 mm and extends substantially perpendiculary between respective surfaces of said shear force collecting plate and said multi-axis torsional sensor to substantially isolate said sensor from said fluid flow.

3. The sensor according to claim 1, wherein said multi-axis torsional sensor is a piezoelectric torsional strain sensor.

4. The sensor according to claim 1, wherein said torsional sensor is a semiconductor material made of silicon.

5. The sensor according to claim 4, wherein said torsional sensor includes at least one hinge integrated in said semiconductor material with selective doped portions thereof and having electrical contacts disposed thereon.

6. The sensor according to claim 4, wherein said torsional sensors further includes two hinges orthogonally arranged with respect to one another, said two hinges forming said connection between said torsional sensor and said arm.

7. The sensor according to claim 2, further including a single crystal silicon having said piezoelectric sensor disposed thereon whereby said sensor produces an electrical output in response to electrical current input, said output signal being proportional to the strain induced on an associated hinge of said torsional sensor.

8. The sensor according to claim 5, wherein portions of said semi-conducting material are etched to define said hinges.

* * * * *